(12) United States Patent
Ferroni et al.

(10) Patent No.: US 11,491,014 B2
(45) Date of Patent: Nov. 8, 2022

(54) MOULD FOR MAKING A TEMPORARY PROSTHETIC COMPONENT FOR A KNEE

(71) Applicant: G21 S.R.L., San Possidonio (IT)

(72) Inventors: Nicola Ferroni, Porto Garibaldi (IT); Filippo Foroni, Mirandola (IT); Filippo Villani, Modena (IT); Francesco Baldacci, Cesena (IT)

(73) Assignee: G21 S.R.L., San Possidonio (IT)

( * ) Notice: Subject to any disclaimer, the term of this patent is extended or adjusted under 35 U.S.C. 154(b) by 589 days.

(21) Appl. No.: 16/587,175

(22) Filed: Sep. 30, 2019

(65) Prior Publication Data

US 2020/0100900 A1 Apr. 2, 2020

(30) Foreign Application Priority Data

Oct. 2, 2018 (IT) .......................... 102018000009088

(51) Int. Cl.
*A61F 2/30* (2006.01)
*A61F 2/36* (2006.01)
*A61F 2/38* (2006.01)
*B29C 45/14* (2006.01)

(52) U.S. Cl.
CPC ............ *A61F 2/3094* (2013.01); *A61F 2/389* (2013.01); *B29C 45/14065* (2013.01); *A61F 2002/30672* (2013.01); *A61F 2002/30957* (2013.01); *A61F 2002/30975* (2013.01); *A61F 2002/3611* (2013.01); *A61F 2310/00353* (2013.01); *B29C 2045/14147* (2013.01)

(58) Field of Classification Search
CPC .................. A61F 2/3094; A61F 2/4684; A61F 2002/30957; A61F 2002/30975; A61F 2002/30672; A61F 2002/30677; B29C 45/14065; B29C 45/64; B29C 2045/14147
See application file for complete search history.

(56) References Cited

U.S. PATENT DOCUMENTS

| | | | |
|---|---|---|---|
| 6,155,812 A * | 12/2000 | Smith ...................... | A61F 2/38 249/55 |
| 7,429,346 B2 * | 9/2008 | Ensign ..................... | A61F 2/38 623/20.14 |
| 9,944,000 B2 * | 4/2018 | Smith ..................... | A61F 2/3094 |
| 2010/0102484 A1 | 4/2010 | Haney et al. | |
| 2013/0183398 A1 | 7/2013 | Haney et al. | |
| 2015/0061181 A1 | 3/2015 | Haney et al. | |
| 2015/0343684 A1 | 12/2015 | Smith et al. | |

(Continued)

FOREIGN PATENT DOCUMENTS

| WO | 2012158618 A1 | 11/2012 |
|---|---|---|
| WO | 2017125832 A1 | 7/2017 |

*Primary Examiner* — Brian A Dukert
(74) *Attorney, Agent, or Firm* — Pearne & Gordon LLP (57) ABSTRACT

Described is a mould (1) for making a temporary prosthetic component for a knee in an operating room comprising: a first half-mould (10); a second half-mould (20) which can be coupled to the first half-mould (10) for forming a moulding chamber (C) for a temporary prosthetic component made of medical cement; and elements (30) for fixing the first half-mould (10) to the second half-mould (20).
Each fixing element (30) has a rod (31) configured for connecting the first half-mould (10) to the second half-mould (20) and defining a weakness neck (32) configured to allow a facilitated breakage of the rod (31).

15 Claims, 6 Drawing Sheets

(56) References Cited

U.S. PATENT DOCUMENTS

2017/0333191 A1 11/2017 Foroni et al.
2018/0290354 A1 10/2018 Smith et al.
2019/0015210 A1 1/2019 Mantovani et al.

* cited by examiner

MOULD FOR MAKING A TEMPORARY PROSTHETIC COMPONENT FOR A KNEE

This invention relates to the field of prosthetics for the knee and, in particular, relates to a mould for making a temporary prosthetic component for a knee in an operating room, a relative method and a kit for making a temporary articulated spacer for a knee in an operating room comprising one or more of these moulds.

The temporary articulated spacers are basically provisional articular prostheses which are used to maintain the correct distance between the respective bones, in the case of the knee between the femur and the tibia, and give a certain degree of articular mobility in view of the application of a permanent prosthesis.

This type of spacer is used, for example, when it is necessary to remove a articular prosthesis due to an infection, which even nowadays has a significant adverse effect in the case of knee prostheses.

When the infection is particularly serious, it is necessary to remove the prosthesis to cure the infection by means of antibiotic therapy before insertion of a new permanent prosthesis.

During the duration of the antibiotic therapy, the provisional spacers are inserted in place of the prosthesis to keep the correct bone distance before insertion of a new permanent prosthesis.

The temporary spacers are also impregnated with antibiotics in such a way as to release them gradually into the infected area after their application, thus contributing to curing the infection.

Recently, temporary spacers have been introduced comprising two components which are applicable, respectively, to the femur and the tibia and which can be coupled in such a way as to allow at least a certain degree of articulated mobility to the knee.

This type of spacer may be made of cement-based material by moulding directly in the operating room.

Currently, the moulding of spacers in the operating room is subject to various problems, including imprecisions and defects in the prosthetic components made, poor possibility of adapting the prosthetic components to the shape of the patient's knee and relatively long times for preparing the spacer during the operation.

In this context, the technical purpose which forms the basis of the invention is to provide a mould for making a temporary prosthetic component for a knee in an operating room, a relative kit and a relative method which overcome at least some of the above-mentioned drawbacks of the prior art.

In particular, the aim of the invention is to provide a mould for making a temporary prosthetic component for a knee in an operating room, a relative kit and a relative method which are able to allow the moulding in an operating room of prosthetic components in a fast, precise and efficient manner.

The technical purpose indicated and the aims specified are substantially achieved by a mould for making a temporary prosthetic component for a knee in an operating room, a relative kit and a relative method comprising the technical features described in one or more of the appended claims. The dependent claims correspond to possible different embodiments of the invention.

Further features and advantages of the invention are more apparent in the non-limiting description which follows of a preferred non-limiting embodiment of a mould for making a temporary prosthetic component for a knee in an operating room, a relative kit and a relative method.

The description is set out below with reference to the accompanying drawings which are provided solely for purposes of illustration without restricting the scope of the invention and in which.

The invention relates to a mould for making a temporary prosthetic component for a knee in an operating room, denoted in the accompanying drawings by the numeral 1 and referred to below simply as "mould 1".

Figure 1:
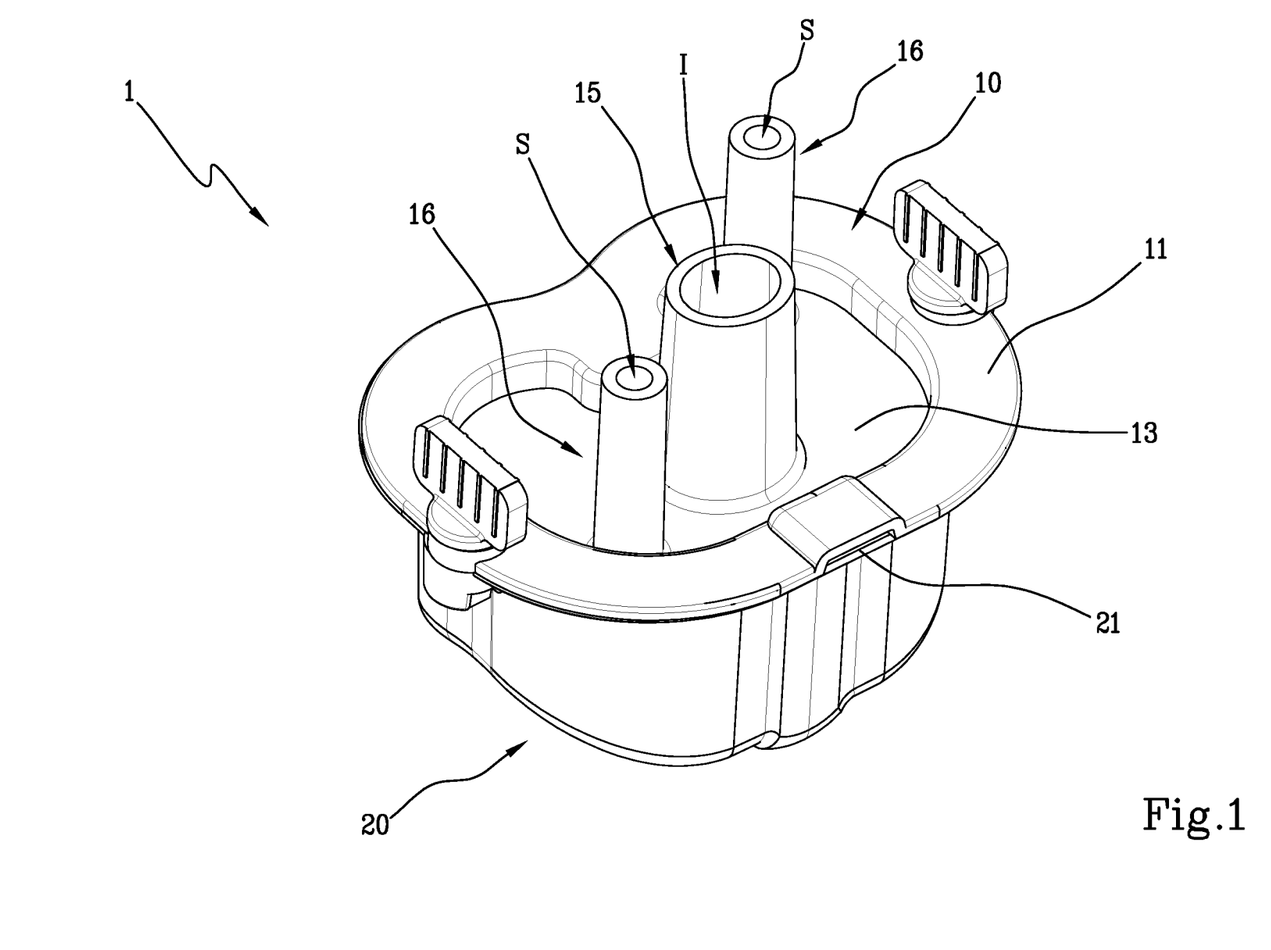
FIG. 1 is a perspective view of a mould for making a temporary prosthetic component for a knee in an operating room made according to the invention.
Figure 2:
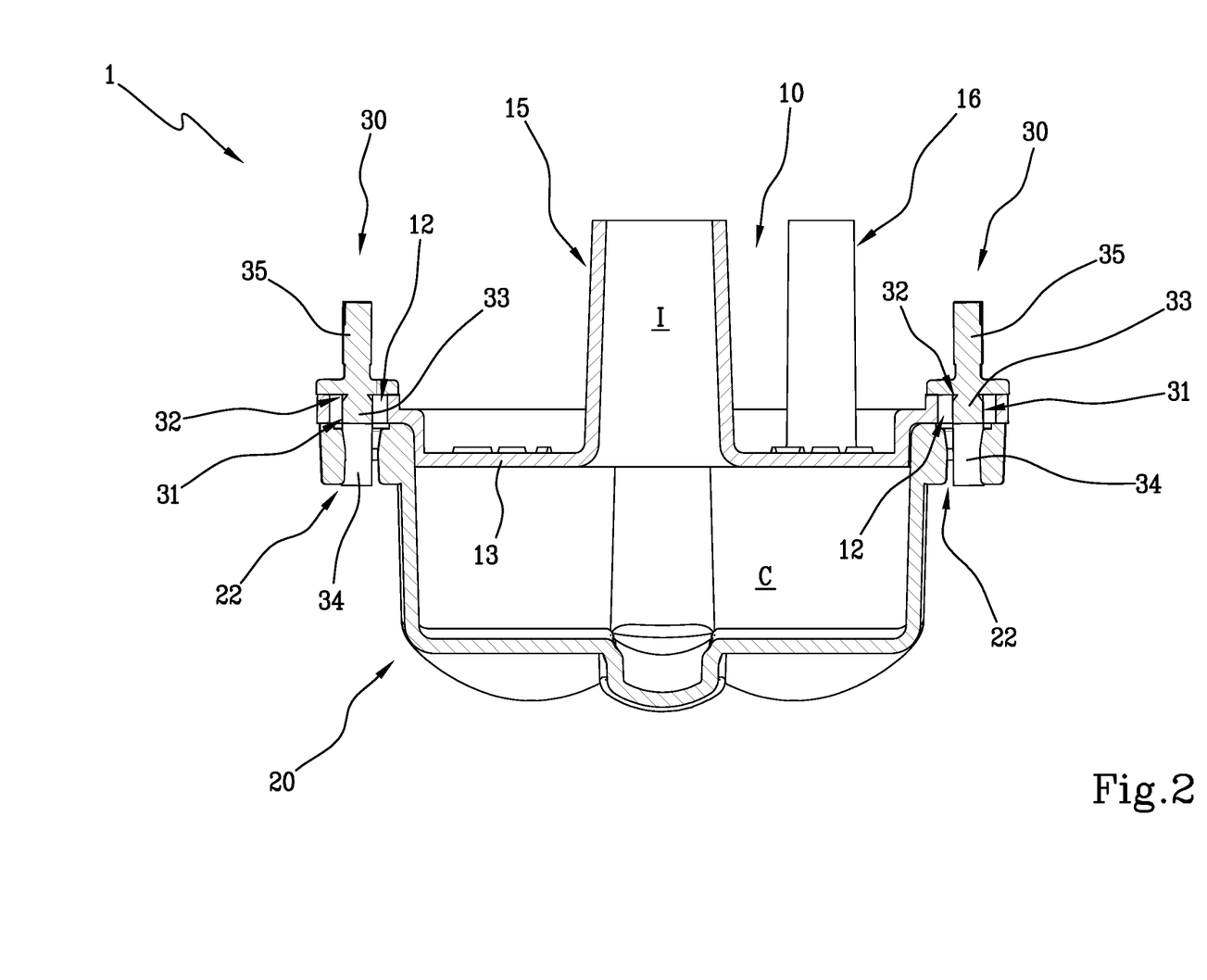
FIG. 2 is a cross-section of FIG. 1.
Figure 6:
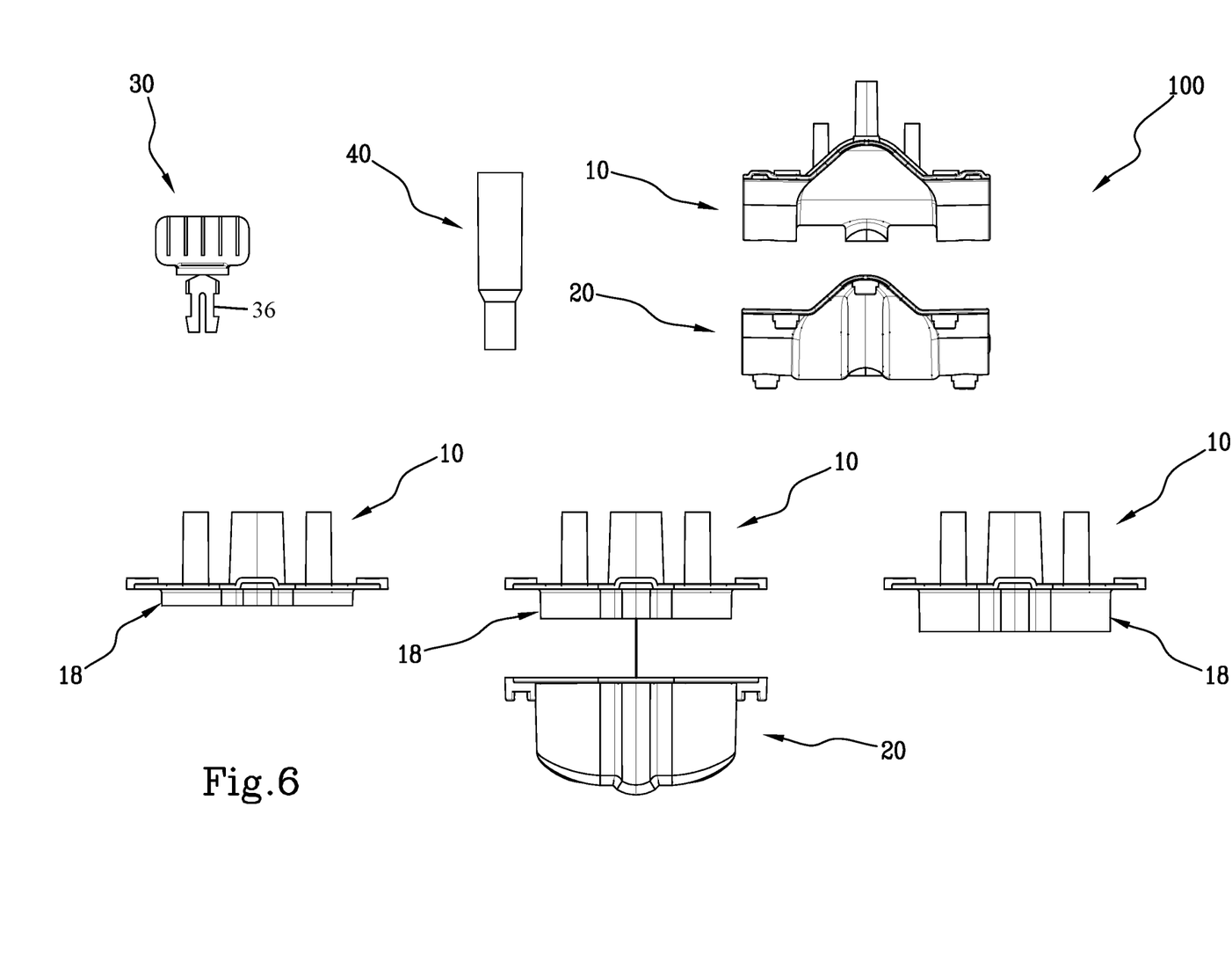
FIG. 6 is a front view of a kit for making a temporary articulated spacer for a knee in an operating room made according to the invention.

In particular, according to an embodiment illustrated in FIGS. 1, 2 and 6, the mould 1 is configured for making a tibial prosthetic component. This solution is referred to below as "tibial mould 1".

Figure 3:
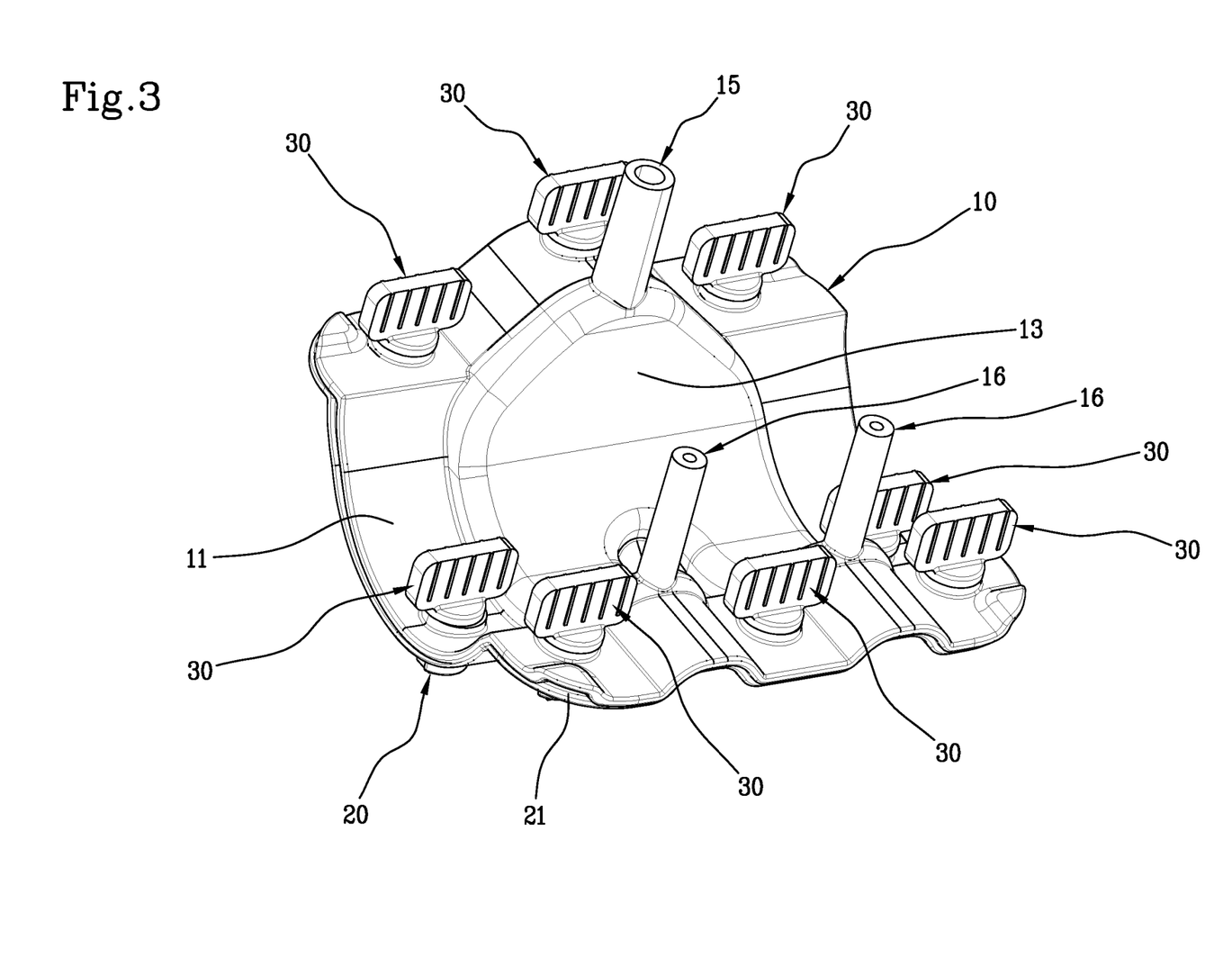
FIG. 3 is a perspective view of a different embodiment of a mould for making a temporary prosthetic component for a knee in an operating room made according to the invention.
Figure 4:
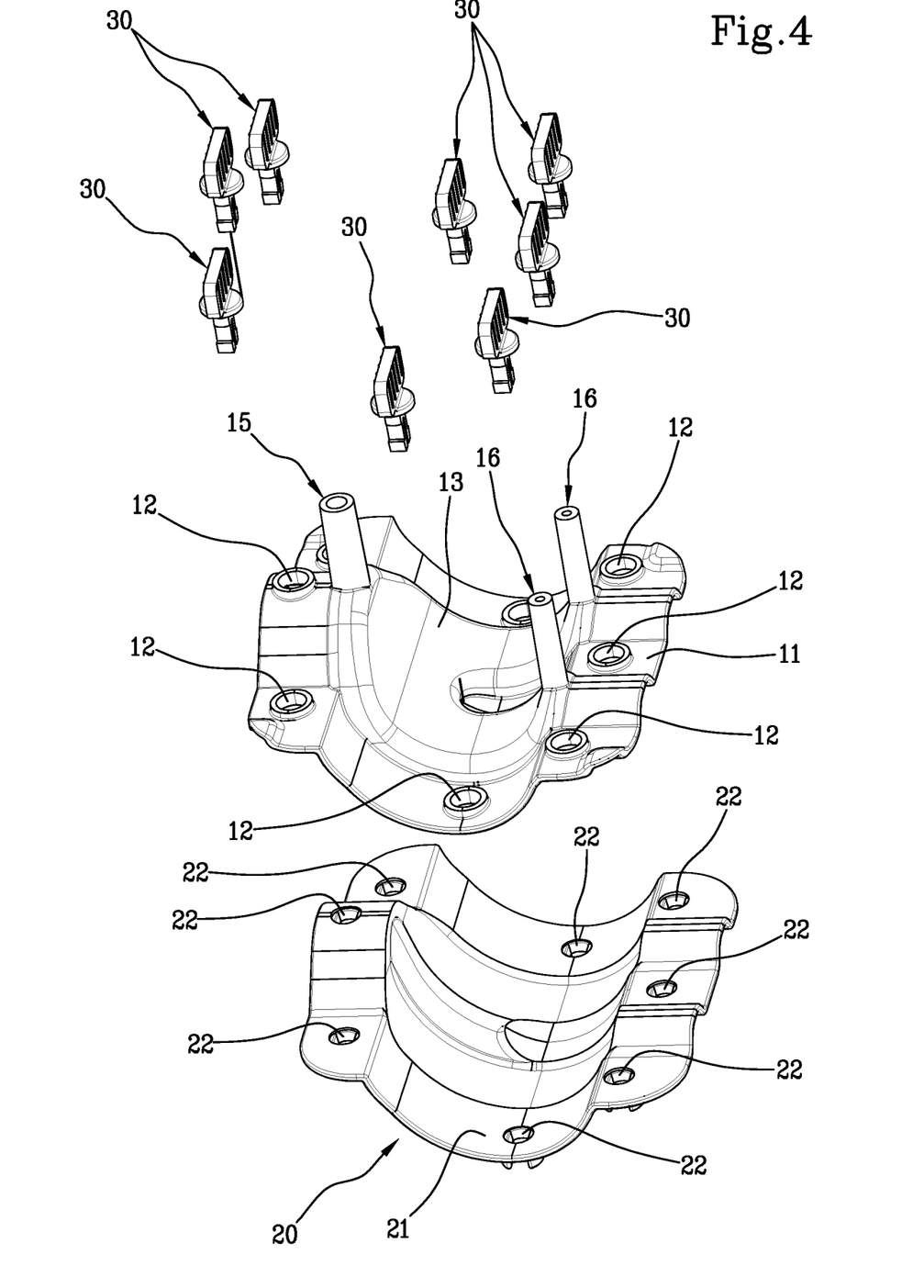
FIG. 4 is an exploded perspective view of the mould of FIG. 3.
Figure 5:
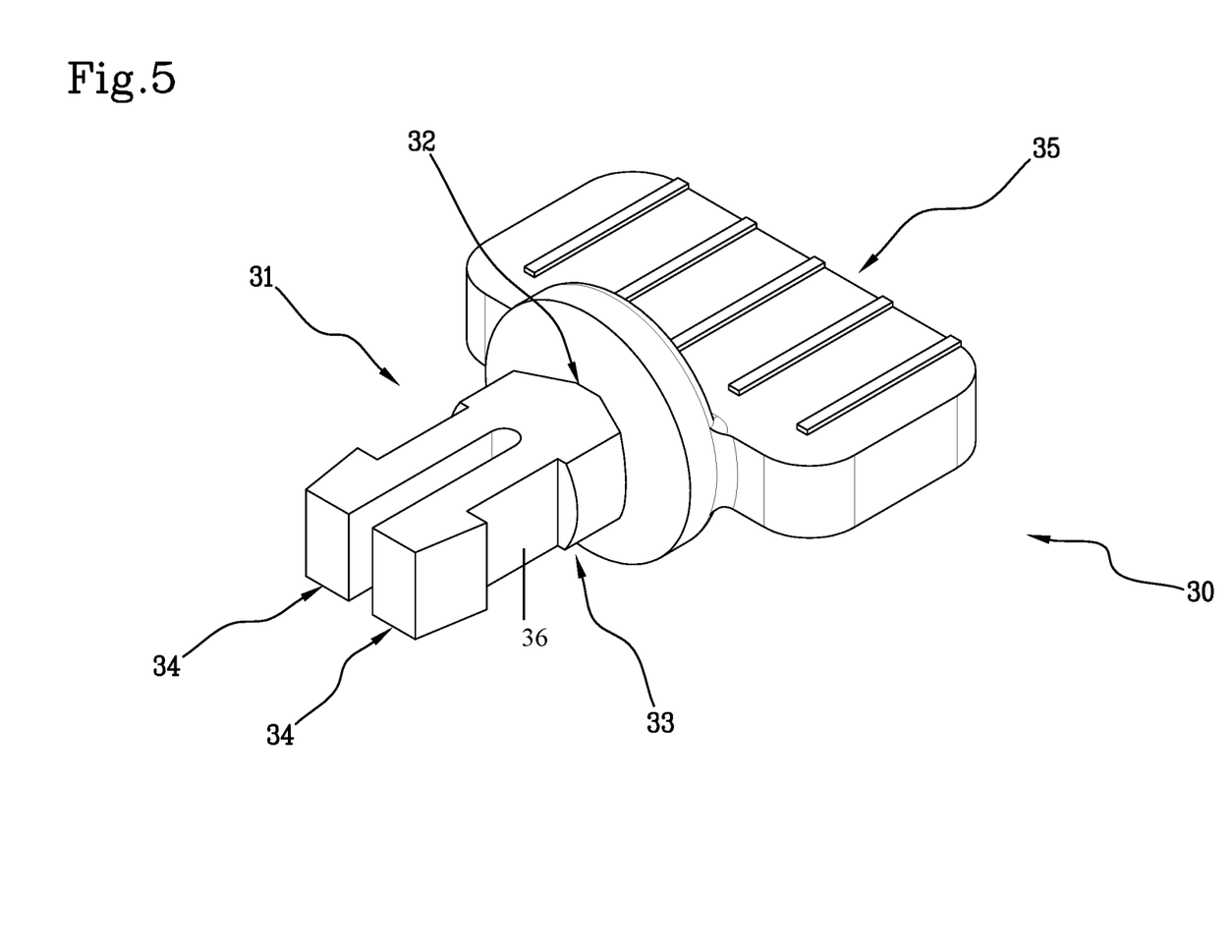
FIG. 5 is a perspective view of a component of the moulds of FIG. 1 and FIG. 3.

According to a different embodiment illustrated in FIGS. 3, 4 and 6, the mould 1 is configured for making a femoral prosthetic component. This solution is referred to below as "femoral mould 1.

All the features described below with reference to the mould 1 refer both to the tibial mould 1 and to the femoral mould 1.

The mould 1 comprises a first half-mould 10 and a second half-mould 20 which can be coupled to each other in contact in a predetermined reciprocal position to define internally a moulding chamber "C".

The moulding chamber "C" is configured to receive a dose of medical cement in the liquid state and allow the solidification to form a temporary prosthetic component.

In particular, the moulding chamber "C" of the tibial mould 1 is configured for moulding a temporary prosthetic tibial component which can be connected to a tibia to replace the proximal epiphysis, whilst the moulding chamber "C" of the femoral mould 1 is configured for moulding a temporary prosthetic femoral component which can be connected to a femur to replace the distal epiphysis.

Preferably, the first and the second half-moulds 10 and 20 have respective coupling flanges 11 and 21 configured for reciprocally moving alongside each other and defining the reciprocal position and orientation for the coupling between the two half-moulds 10 and 20.

Preferably, the first and second half-moulds 10 and 20 have a plurality of holes 12 and 22 distributed along the respective flanges 11 and 21 in such a way as to be positioned alongside and coaxial with the positioning alongside of the first and second half-moulds 10 and 20 in the predetermined reciprocal position.

Preferably, the first and second half-moulds 10 and 20 define a non-circular shape of each hole 12 and 22 and in particular having two flat surfaces parallel to and facing opposite sides of the respective hole 12 and 22.

Moreover, the flanges 11 and 21 preferably have reinforcement portions with a greater thickness which surround the holes 12 and 22.

More in detail, the first half-mould 10 preferably has a wall 13 defining a surface of the moulding chamber "C" and surrounded by the flange 11. Moreover, the first half-mould 10 has a first tubular body 15 preferably cylindrical which protrudes from the wall 13 and defines an injection duct "I" configured to allow an introduction of cement-based material in the moulding chamber "C".

In the case of the tibial mould 1, the injection duct "I" has a tapered shape and acts in conjunction with the moulding chamber "C" for forming and solidifying the tibial prosthetic component.

In particular, the moulding chamber "C" is configured to allow the solidification of a main or "end" portion of the prosthetic component, which defines the zone of the joint touched by the mobile contact.

The injection duct "I" is, on the other hand, configured to allow the solidification of an engagement pin extending from the main portion in such a way as to allow the fixing to the bone stump.

Vice versa, in the case of the femoral mould 1, the tubular body 15 has a portion for connection with the wall 13 configured for a facilitated breakage designed to allow a manual detachment of the wall.

Preferably, the first half-mould 10 also has one or more second tubular bodies 16, preferably exactly two, which protrude from the wall 13 and define respective vent ducts "S" configured to allow the escape of air and excess cement-based material from the moulding chamber "C" during the introduction into the latter of cement-based material.

Preferably, each second tubular body 16 (belonging both to the tibial and femoral mould 1) has a portion for connection to the wall 13 configured for a facilitated breakage designed to allow a manual detachment of the wall. More specifically, the failure may be determined by manually gripping each first and/or second tubular body 15 and 16 and bending it in such a way as to act on the respective connecting portion.

The mould 1 also comprises fixing elements 30 configured for connecting in contact with each other the first half-mould 10 to the second half-mould 20.

Each fixing element 30 has a rod 31 configured for connecting the first half-mould 10 to the second half-mould 20.

In particular, each rod 31 is configured to engage respective holes 12 and 22 of the first and second half-moulds 10 and 20 positioned in a position alongside each other in such a way as to determine a reciprocal compression of the first and second half-moulds 10 and 20 in the coupling position.

Advantageously, each rod 31 defines a weakness neck 32 configured to allow a facilitated breakage of the rod 31.

Preferably, each fixing element 30 comprises a gripping portion 35 connected to the rod 31 and configured to allow a user to manually impart a torsion at a relative end.

According to the embodiment illustrated, the gripping portion 35 has a coupling surface configured for making contact on a surface of a respective half-mould 10 or 20 for defining a plane of rotation of the gripping portion 35 relative to the respective half-mould 10 or 20. Preferably, the rod 31 defines the neck 32 at a relative connecting portion with the gripping portion 35, in such a way that the twisting imparted on the gripping portion 35 discharges directly on the neck 32.

Preferably, each rod 31 is configured to engage the respective holes 12 and 22 with a clip coupling preferably of the irreversible type, in such a way that following coupling the first and the second half-moulds 10 and 20 can be separated only by breaking all the necks 32.

According to the preferred embodiment, each rod 31 has a central portion 33 connected to the neck 32 in such a way that the neck 32 is interposed between the central portion 33 and the gripping portion 35 and a plurality of flexible elements 34 connected to the central portion 33 and protruding in the opposite direction to the neck 32 to define the clip coupling of the respective fixing element 30 in the respective holes 12 and 22.

Preferably, each rod 31 has a ratio between the cross-section surface of the neck 32 and of the central portion 33, measured normally to a main direction of extension of the rod 31, of between 0.1 and 0.5 and even more preferably between 0.25 and 0.40.

Preferably, the first and/or second half-moulds 10 and 20 define respective coupling portions, in particular at the holes 12 and/or 22, which have a shape coupling with a lateral surface 36 of each rod 31 in such a way as to constrain it rotationally.

This coupling makes it possible to rotationally lock the rods 31 during twisting of the head portions 35 to determine a torsional force in the neck 32 sufficient to determine the relative failure.

Preferably, each rod 31 has a non-circular shape in plan view and is configured to determine the shape coupling with the holes 12 and 22, in turn, non-circular. Preferably, each rod 31 has a plan shape substantially shaped to match that of the respective holes 12 and 22.

In particular, the lateral surface 36 comprises two flat surfaces parallel to each other shaped to match the flat surfaces described above of the respective holes 12 and 22.

Preferably, the holes 12 and 22 and the fixing elements 30 are configured to allow an insertion of the rods 31 in the holes 12 and 22 in such a way that the gripping portions 35 protrude from the mould 1 in the same direction as the tubular bodies 15 and 16, in such a way as to allow a rapid destruction of the fixing elements 30 and of the tubular bodies 15 and 16. Another object of the invention is a kit for making a temporary articulated spacer for a knee in an operating room, illustrated in FIG. 6 and denoted by the numeral 100.

The kit 100 comprises a tibial mould 1 and a femoral mould 1 configured for the moulding, respectively, of a temporary prosthetic tibial and femoral component, which can be coupled together to define a temporary articulated spacer which allows the bending of the knee.

Preferably, the kit 100 comprises a plurality of first and/or second half-moulds 10 or 20 which are different in size, which can be selectively coupled to the first and/or second half-moulds 10 or 20 of the tibial and/or femoral moulds 1 of the kit 100 for dimensionally adjusting the respective moulding chamber "C".

Preferably, the selection of the first and/or second half-moulds 10 or 20 allows adjustment of the thickness of the moulding chamber "C" relative to a direction of extension of the respective prosthetic component.

More specifically, according to the preferred embodiment, the second half-mould 20 of the tibial mould 1 has a tray-shaped concave form and defines an internal space and an access opening.

The kit 100 also comprises a plurality of first half-moulds 10, which can be coupled to the single second half-mould 20 of the tibial mould 1, which have respective coupling portions 18 configured to engage the opening and partly occupy the inner space to define the moulding chamber "C". More specifically, the first half-moulds 10 have coupling portions 18 of different sizes in such a way as to each define a moulding chamber "C" of different dimensions.

According to the embodiment of FIG. 6 the coupling portions 18 are protrusions extending normally to the flange 11 and having a height different to each other measured away from the respective flange 11. Preferably, the first tubular body 15 of the femoral mould 1, being removable by manual breaking, has a diameter less than the first tubular body 15 of the tibial mould 1, which defines the engagement pin of the corresponding prosthetic component.

Preferably, the kit according to the invention comprises a tubular adapter 40 configured for connecting a spout of a syringe for dispensing liquid cement-based material to the first tubular body 15 of the femoral mould 1 by shape coupling.

It should be noted that the kit can be made available to the users with the half-moulds 10, 20 already coupled by means of the above-mentioned fixing elements 30 (or "closing clips") and it is also possible to provide further clips 30 to allow the clamping of the spacer once the adequate height has been established; the kit can therefore be provided including ten clips 30, which represent the sufficient number for its complete use. Advantageously, according to a possible but non-binding embodiment of the invention, the spout of a dispensing syringe is shaped in such a way as to have a shape coupling with the first tubular body 15 of the tibial mould 1 and the adapter 40 allows use of the syringe for injecting the cement-based material in both the moulds 1.

Preferably, the adapter 40 is configured to remain engaged in the first tubular body 15 of the femoral mould 1 after dispensing the cement-based material, detaching from the spout of the dispensing syringe and, after solidifying the latter, is configured to be used by a user as a lever for manually breaking the corresponding connecting portion of the first tubular body 15.

Another object of the invention is a method for making a temporary prosthetic component for a knee in an operating room.

The method according to the invention comprises a preliminary step of preparing a mould 1 of the type described above and a further preliminary step of preparing a dose of medical cement-based material, preferably with the addition of antibiotic substances and preferably in such a way that the fluid phase of the medical cement has a low viscosity.

Preferably, the cement-based material is based on polymethylmethacrylate (PMMA) and has the addition of BaSO4 as a radio-opaque agent.

The method comprises a further step of joining the first and the second half-moulds 10 and 20 using the fixing elements 30 to define the moulding chamber "C".

Subsequently, the method comprises a step of introducing medical cement-based material into the moulding chamber "C".

Preferably, this step comprises connecting a spout of a dispenser of cement-based material to the first tubular body 15 described above to place it in communication with the injection duct "I" of the mould 1. Moreover, the method comprises a subsequent step of waiting for the at least partial solidification of the cement-based material of the moulding chamber "C".

In the case of a femoral mould 1, the method preferably comprises a step of removing the first tubular body 15 destroying the connecting portion, preferably by manually levering on the adapter 40 connected to it. Preferably, the method comprises a further step of removing the second tubular bodies 16 destroying the respective connecting portions preferably by manually levering the second tubular bodies 16.

Advantageously, the method comprises a step of destroying the fixing elements 30 and in particular the respective necks 32.

Preferably, this step comprises a twisting action, preferably manual, on the respective gripping portions 35 of the fixing elements 30.

The method then comprises a step of mutually separating the first and second half-moulds 10 and 20 and extracting the temporary prosthetic component from them.

Another object of the invention is a method for making a temporary articulated spacer in an operating room, preferably which can be implemented using the kit 100 described above.

The method comprises a first execution of the steps described relative to the method for making a temporary prosthetic component for a knee in an operating room as described above for making a temporary prosthetic tibial component (using a tibial mould 1), and a second execution of the same steps for making a temporary prosthetic femoral component (using a femoral mould 1).

Advantageously, the step of preparing the tibial mould 1 comprises a step of selecting a first half-mould 10 between various different first half-moulds 10 having coupling portions 18 with different dimensions as a function of a desired size of the respective temporary prosthetic tibial component.

The invention achieves the set aim by overcoming the drawbacks of the prior art.

In fact, the moulds described have simple and economical components to be produced and can be used quickly in the operating room for moulding the relative prosthetic components.

Advantageously, the configuration of the fixing elements allows a fast and stable coupling of the first and the second half-moulds and a rapid destruction of them to separate the first and the second half-moulds. Moreover, the possibility of removing the first and/or the second tubular bodies allows the risk of damage to the prosthetic component during separation of the first and second half-moulds to be reduced.

Moreover, the modularity of the kit described above allows a dimensional adjustment of the prosthetic component to be performed in a simple manner in the operating room on the basis of the needs of the customer.

The invention claimed is:

1. A mould (1) for making a temporary prosthetic component for a knee in an operating room, comprising:
   a first half-mould (10);
   a second half-mould (20) which can be coupled to the first half-mould (10) to form a moulding chamber (C) for a temporary prosthetic component made of medical cement;
   elements (30) for fixing the first half-mould (10) to the second half-mould (20);
   characterised in that
   each fixing element (30) has a rod (31) configured for connecting the first half-mould (10) to the second half-mould (20) and defining a weakness neck (32) configured to allow a facilitated breakage of the rod (31),
   the first and second half-moulds (10, 20) have respective flanges (11, 21) which can be coupled to each other, the fixing elements (30) being configured to engage with respective holes (12, 22) made in the opposite flanges (11, 21) to join the first and second half-moulds (10, 20).

2. The mould (1) according to claim 1, wherein the holes (12, 22) of the first and/or second half-mould (10, 20) have respective coupling portions having a shape coupling with a lateral surface (36) of each rod (31) in such a way as to rotationally constrain each rod (31) to the first and/or second half-mould (10, 20).

3. The mould (1) according to claim 1, wherein each fixing element (30) comprises a gripping portion (35) connected to the rod (31) and configured to allow a user to manually impart a torsion acting on the neck (32).

4. The mould (1) according to claim 3, wherein the rod (31) is connected to the gripping portion (35) at the neck (32).

5. The mould (1) according to claim 1, wherein each rod (31) is configured for a clip fastening in a respective one of the holes (12, 22) and has a non-circular shape configured to match with the holes (12 and 22) which are also not circular.

6. The mould (1) according to claim 1, wherein the first half-mould (10) has:
- a wall (13) defining a surface of the moulding chamber (C);
- a first tubular body (15) protruding from the wall (13) and defining an injection duct (I) configured to allow an introduction of cement-based material in the moulding chamber (C);
- one or more second tubular bodies (16) protruding from the wall (13), each second tubular body (16) defining a venting duct (S) configured to allow the escape of air and excess cement-based material from the moulding chamber (C);

each second tubular body (16) having a connecting portion with the wall (13) configured for a facilitated breakage designed to allow a manual detachment of the respective second tubular body (16) from the wall (13).

7. The mould (1) according to claim 6, wherein the moulding chamber (C) is configured to allow the solidification of a main portion of the prosthetic component and the injection duct (I) is configured to allow the solidification of an engagement pin protruding from the main portion.

8. The mould (1) according to claim 6, wherein the first tubular body (15) has a connecting portion with the wall (13) configured for a facilitated breakage designed to allow a manual detachment of the first tubular body (15) from the wall (13).

9. A kit (100) for making a temporary articulated spacer for a knee in an operating room, comprising:
- a tibial mould (1) and a femoral mould (1), both being according to claim 1;
- the tibial mould (1) a configured for moulding a temporary prosthetic tibial component, which can be connected to a tibia for replacing the proximal epiphysis;
- the femoral mould (1) configured for moulding a temporary prosthetic femoral component, which can be connected to a femur for replacing the distal epiphysis;
- the temporary prosthetic femoral and tibial components being connectable to each other for defining a temporary articulated spacer which can be applied to a knee.

10. The kit (100) according to claim 9, comprising a plurality of first and/or second half-moulds (10, 20) of variable size, which can be selected for dimensionally adjusting the moulding chamber (C) of the tibial and/or femoral mould (1).

11. The kit (100) according to claim 10, wherein the second half-mould (20) of the tibial mould (1) has a concave shape defining an inner space and an opening giving access to the inner space, the kit (100) comprising a plurality of first half-moulds (10) having respective coupling portions (18) configured to engage the opening and partly occupy the inner space to define the moulding chamber (C) during the coupling with the second half-mould (20), the first half-moulds (10) having respective coupling portions (18) with different dimensions.

12. A method for making a temporary prosthetic component for a knee in an operating room, comprising the following steps:
- preparing a mould (1) in accordance with claim 1, comprising a first half-mould (10) and a second half-mould (20);
- joining the first and the second half-mould (10, 20) by means of fixing elements (30) to define a moulding chamber (C) for a temporary prosthetic component;
- introducing cement-based medical material in the moulding chamber (C);
- waiting for an at least partial solidification of the cement-based material;
- destroying the fixing elements (30);
- mutually separating the first and the second half-moulds (10, 20).

13. The method according to claim 12, wherein the step of destroying the fixing elements (30) comprises twisting respective gripping portions (35) of the fixing elements (30).

14. The method according to claim 12, wherein the step of introducing cement-based material comprises connecting a tubular adapter (40) to a first tubular body (15) protruding from a wall (13) of the first half-mould (10).

15. A method for making a temporary articulated spacer in an operating room, comprising:
- performing a first method and a second method, both according to claim 12;
- the first method being for making a temporary prosthetic tibial component, wherein the step of preparing a mould (1) comprises a step of selecting a first and/or a second half-mould (10, 20) as a function of a desired size of the temporary prosthetic tibial component;
- the second method being for
- making a temporary prosthetic femoral component wherein, after at least partial solidification of the cement-based material, the method comprises a step of destroying a connecting portion between a first tubular body (15) and a wall (13) for removing the first tubular body (15).

* * * * *